United States Patent [19]

Datta et al.

[11] 4,168,268

[45] Sep. 18, 1979

[54] PROCESS FOR ISOLATING THIENAMYCIN

[75] Inventors: Rathin Datta, Princeton; George T. Wildman, Westfield, both of N.J.

[73] Assignee: Merck & Co., Inc., Rahway, N.J.

[21] Appl. No.: 936,549

[22] Filed: Aug. 24, 1978

Related U.S. Application Data

[63] Continuation of Ser. No. 773,354, Mar. 1, 1977, abandoned.

[51] Int. Cl.$^2$ ............................................. C07D 487/04
[52] U.S. Cl. ............................... 260/326.31; 424/124
[58] Field of Search ..................... 195/80 R; 424/124; 260/326.31, 326.27

[56] References Cited

U.S. PATENT DOCUMENTS

| | | | |
|---|---|---|---|
| 3,467,654 | 9/1969 | McCormick | 260/243 C |
| 3,725,400 | 4/1973 | Voser | 260/243 C |
| 3,853,863 | 12/1974 | Jackson et al. | 260/243 C |
| 3,950,357 | 4/1976 | Kahan et al. | 260/326.31 |
| 4,000,161 | 12/1976 | Goegelman et al. | 260/326.31 |

OTHER PUBLICATIONS

Friedrich Helfferich, *Ion Exchange*, McGraw-Hill Book Company, 1962, pp. 19-21 and 584.

*Primary Examiner*—Raymond N. Jones
*Assistant Examiner*—Robert J. Warden
*Attorney, Agent, or Firm*—Hesna J. Pfeiffer; Richard A. Thompson; Julian S. Levitt

[57] ABSTRACT

Fermentation broths or impure solutions containing thienamycin, a substance having antibiotic activity against gram-negative and gram-positive microorganisms, are isolated using liquid ion exchange systems.

4 Claims, No Drawings

PROCESS FOR ISOLATING THIENAMYCIN

This is a continuation, application Ser. No. 773,354, filed Mar. 1, 1977 now abandoned.

BACKGROUND OF THE INVENTION

The antibiotic, thienamycin, is obtained by growing strains of *Streptomyces cattleya* microorganism in suitable aqueous nutrient media under controlled conditions. The present invention is directed to the methods for recovering the antibiotic in substantially pure form.

A process for the isolation of the antibiotic thienamycin is reported in U.S. Pat. No. 3,950,357. Said process utilizes solid resin ion exchangers.

Moreover, thienamycin is a hydrophilic, amphoteric compound which cannot be extracted from aqueous solutions by simple organic solvents. Hence, simple solvent extraction which is highly applicable to the isolation of penicillin and other antibiotics cannot be readily applied here.

SUMMARY OF THE INVENTION

The novel process described herein uses water insoluble liquid ion exchangers which are dissolved in suitable organic solvents to transfer the thienamycin by the mechanism of ion exchange from the aqueous phase to the organic solvent followed by transfer of purified thienamycin from the liquid ion exchange/solvent system into suitable aqueous buffers, again by the mechanism of ion exchange. The use of conventional centrifugal extractors for the ion exchange extraction process lead to extremely fast mixing and phase separations thereby minimizing the time that thienamycin is under adverse pH conditions. This results in higher thienamycin recoveries than obtained by the use of conventional solid ion exchangers.

This invention relates to the method for recovering and purifying the antibiotic compound, thienamycin, having the following structural formula:

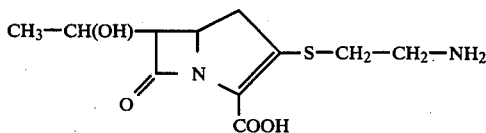

from fermentation broths in which the antibiotic is produced or from solutions containing partially purified antibiotic. This is achieved by contacting the fermentation broth in which the antibiotic is produced or a solution of partially purified antibiotic with liquid ion exchanger dissolved in an organic solvent to transfer the antibiotic into the liquid ion exchange system (forward extraction) and thereafter contacting the liquid ion exchange system which contains the antibiotic with an aqueous buffer solution to affect the transfer of the antibiotic into the aqueous buffer phase (back extraction).

Substantial purification of the antibiotic occurs in the liquid ion exchange processes. The antibiotic of Formula I may also be further purified by a desalting and chromatography on polymeric adsorbants such as Amberlite XAD-1, 2 and 4, preferably XAD-2, (manufactured by Rohm and Haas Co., Philadelphia, Penna.) chromatography on strong cation or anion exchange resins such as Dowex 50×2 (Na+ cycle) or Dowex 1×2 (Cl⊖ cycle) (manufactured by Dow Chemical Co., Midland, Mich.) and by gel permeation chromatography through polyacrylamide gels.

The principal advantages of the liquid ion exchange process over the conventional solid ion exchange process are: (1) higher thienamycin recovery; and (2) the process can be operated in a truly continuous mode, thus giving the economic advantages of a continuous operation.

DESCRIPTION OF THE PREFERRED EMBODIMENTS

Thienamycin is produced during the aerobic fermentation of suitable aqueous nutrient media, under controlled conditions, by a strain of *Streptomyces cattleya* capable of producing said compound such as *Streptomyces cattleya* NRRL 8057. Aqueous media, such as those employed for the production of other antibiotics are suitable for producing thienamycin. Such media contain sources of carbon, nitrogen and inorganic salts assimilable by the microorganism.

The production and characterization of the antibiotic thienamycin is described in U.S. Pat. No. 3,950,357 and is incorporated herein by reference.

The novel process utilized herein is based on liquid ion exchangers and an organic solvent. More particularly, the ion exchangers are liquid cation exchangers and liquid anion exchangers.

The liquid cation exchangers utilized in this invention are preferably those of the strong cationic variety such as dinonyl naphthalene sulfonic acid (DNNS) in the hydrogen, sodium or other cycles. The term "cycle" refers to the particular salt form of the liquid ion exchanger moiety. Other strong cationic liquid ion exchangers which can be utilized are didodecylnaphthalene sulfonic acid and its salts. Weaker cationic liquid ion exchangers, such as di-(2-ethylhexyl)phosphoric acid may also be used, however, the strong cationic ion exchangers are preferred.

The cation exchanger is usually utilized in combination with an organic solvent as the extraction system. By the term "organic solvent" is meant an organic solvent or solvent mixture. The organic solvent should be one that has a moderately high dielectric constant.

By the term "moderately high dielectric constant" is meant a dielectric constant from about four to about twenty-four. Representative of such organic solvents having moderately high dielectric constants are straight and branched chain alcohols having from four to ten carbon atoms, straight and branched chain ketones having from four to eight carbon atoms and straight and branched chain esters having from four to ten carbon atoms.

Representative of said alcohols are n-butanol, isobutanol, pentanol, isopentanol, hexanol, heptanol and the like. Representative of said ketones are methyl ethyl ketone, methylisobutyl ketone and the like. Representative of said esters are ethyl acetate, butyl acetate and the like.

When a solvent mixture is utilized, one solvent with a high dielectric constant may be combined with a solvent having a low dielectric constant in order to obtain a solvent mixture having the desired dielectric constant.

By the term, "high dielectric constant" is meant a solvent having a dielectric constant from about twenty-five to about one hundred. By the term, "low dielectric constant" is meant less than four. Also, a mixture of solvents having moderately high dielectric constants may be utilized.

The cation exchanger is usually utilized in a solvent solution wherein the cation exchanger is 2 to 15% by volume. The liquid cation exchange solution is then adjusted to a pH between 1 to 4 with a suitable aqueous buffer.

The liquid anion exchangers are usually salts of strong anionic materials such as quaternary ammonium compounds. The liquid anion exchanger can be a salt of tricaprylyl methyl ammonium such as acetate, sulfate, propionate, phosphate, chloride, and the like or as the hydroxyl form. Other types of liquid anion exchangers that may be utilized are water insoluble primary, secondary and tertiary amines.

The liquid anion exchanger is also more effective when used with a solvent or solvent mixture having a moderately high dielectric constant.

The solvents and solvent mixtures described above which can be utilized with the cation exchanger can also be utilized with the anion exchanger.

The anion exchanger is usually utilized in a solvent solution wherein the anion exchanger is about 5 to 30% by volume.

The process for thienamycin isolation is carried out by contacting the acidified (range from about 2.5-4.5) thienamycin-containing broth or solution with the liquid cation exchange system. After separation of the two liquid phases, the organic phase which now contains the thienamycin is back extracted with an aqueous inorganic buffer such as sodium bicarbonate, ammonium hydroxide, sodium phosphate or potassium phosphate and the like or aqueous pyridine and the thienamycin transfers to the aqueous phase. The aqueous phase is then separated from the organic phase.

The latter thienamycin-containing aqueous phase is made alkaline (range from about 8.0-11.0) and then intimately contacted with the liquid anion exchange system. After separation of the two liquid phases, the organic phase which now contains the thienamycin is back extracted with an aqueous buffer such as sodium acetate, potassium acetate, potassium chloride, hydrogen chloride, or sodium citrate and the like and the thienamycin transfers to the aqueous phase which is then separated from the organic phase.

Further purification of the antibiotic may be obtained by desalting and chromatography on polymeric adsorbent resins like Amberlite XAD-1, 2 and 4, preferably XAD-2, chromatography at neutral pH on strong cation exchange or anion exchange resins such as Dowex 50×2 (Na+ cycle) or Dowex 1×2 (Cl⊖ cycle) and by gel permeation chromatography using polyacrylamide gels.

The process described herein can be utilized with fermentation broths or solutions over a wide range of antibiotic concentrations. In general, the higher the antibiotic concentration, the more efficient the process. For instance, the antibiotic concentration can range from about two milligrams per liter to about ten thousand milligrams per liter. However, this range is not intended to exclude solutions or broths which have been prepared to contain higher concentrations of the antibiotic thienamycin.

One such procedure comprises extracting thienamycin with a strongly acidic liquid cation exchange system at acidic pH, from about 2.5-4.5, (forward extraction), separating the phases and then contacting the organic phase with an aqueous back extractant, separating the phases followed by contacting the latter aqueous phase with a strongly basic liquid anion exchange system at alkaline pH, from about 8.0-11.0, (forward extraction), separating the phases and then contacting the organic phase with another aqueous back extractant and then separating the phases. The latter aqueous solution so obtained can be further purified by the following processes: desalting and chromatography on a polymeric adsorbent, chromatography on an anion exchange resin of the polystyrenequarternary ammonium type or chromatography on a cation exchange resin with a buffer or water; gel filtration and chromatography on an adsorbing resin.

The process of the invention can be carried out wherein either of the liquid ion exchangers is utilized without using the other. Thus, one may utilize the liquid anion exchanger to the exclusion of the liquid cation exchanger, or the liquid cation exchanger can be utilized to the exclusion of the liquid anion exchanger.

However, if both liquid ion exchangers are utilized in sequence, the sequence in which the liquid ion exchangers are utilized is not critical. Thus, one may use the liquid cation exchanger followed by the liquid anion exchanger or the liquid anion exchanger followed by the liquid cation exchanger.

The extractor system utilized in this invention can be any of those well known in the art for the separation of liquids having different densities. Those skilled in the art will appreciate that different centrifuges with varying sizes and shapes will have to be adjusted for optimum results.

EXAMPLE 1

A tube of lyophilized culture containing a thienamycin-producing *Streptomyces cattleya* is opened aseptically and the contents suspended in a 250-ml. baffled Erlenmeyer flask containing 50 ml. of sterile Medium B having the following composition:

| Medium B | |
|---|---|
| Autolyzed yeast type pH | 10 g./l. |
| Dextrose | 10 g./l. |
| Mg . $SO_4 7H_2O$ | 50 mg./l. |
| $KH_2PO_4$ | 0.182 g./l. |
| $Na_2HPO_4$ | 0.19 g./l. |
| pH 6.5 before sterilization | |

The inoculated flask is shaken at 28° C. on a 150 rpm rotary shaker for 24 hours. Three ten-ml. portions of the Medium B stage 24-hour broth are removed asceptically. Each 10-ml. portion is mixed immediately with 500 ml. of Medium B contained in three 2-liter baffled Erlenmeyer flasks. These seed flasks are shaken at 28° C. on a 150 rpm rotary shaker for 24 hours.

Fifteen hundred ml. of the 24-hour Medium B broths contained in the 2-liter baffled Erlenmeyers are used immediately to innoculate a 756-liter stainless steel fermentor containing 467 liters of Medium E having the following composition:

| Medium E | |
|---|---|
| Glycerol | 10 g./l. |
| Pharmamedia | 5 g./l. |
| $CaCl_2—6H_2O$ | 0.01 g./l. |
| Distillers Solubles | 10 g./l. |
| $CaCO_3$ | 3 g./l. |
| Polyglycol 2000 | 2.5 g./l. |

-continued

| Medium E |
| --- |
| pH 7.3 before sterilization |

This tank is operated at 28° C. using an agitation rate of 130 rpm and an airflow of 10 cu. ft. per minute for 48 hours. The pH of the fermentation is monitored at 24-hour intervals and tabulated in the following table.

| Age | pH |
| --- | --- |
| 0 | 6.8 |
| 24 | 6.8 |
| 48 | 6.5 |

Four hundred fifty-four liters of the above 48-hour broth contained in the 756-liter stainless steel fermentor is used immediately to innoculate a 5670-liter stainless steel fermentor containing 4082 liters of Medium G having the following composition:

| Medium G | |
| --- | --- |
| Cornsteep liquor | 15 g./l. |
| Glycerol | 10 g./l. |
| Pharmamedia | 5 g./l. |
| CoCl$_2$ . 6H$_2$O | 0.01 g./l. |
| CaCO$_3$ | 3 g./l. |
| Polyglycol 2000 | 2.5 g./l. |
| pH 7.3 before sterilization | |

This tank is operated at 25° C. using an agitation rate of 0.0154 rpm/liter and an airflow of 0.012 cu. ft./liter for 96 to 100 hours. The batch pH is controlled at 6.0–7.0.

The 4082 liters of fermentation broth is filtered using a 30-inch filter press and a filter aid admix to the extent of 4% w/v. A 12-gram amount of (ethylenedinitrile)-tetra acetic acid, sodium salt is added to the filtrate. The filtrate is cooled to 6° C.

The filtered broth, at about 5° C., is mixed continuously with 2.5 normal sulfuric acid to bring the broth pH to 3 using an in-line mixer. The acidified broth pH 3 is then fed at a rate of 60 gallons per minute (gpm) to a centrifugal extractor where it is contacted with cold (about 5° C.) 10% v/v dinonylnaphthalene sulfonic acid (DNNS) (primarily in the sodium cycle), at pH 2 in n-butanol solution which is being fed to the extractor at 30 gallons per minute. In the extractor, the two solutions are intimately mixed and the cation exchange reaction occurs between the Na$^+$ and H$^+$ ions of the DNNS moiety and the ammonium cation form of thienamycin resulting in the transfer of thienamycin from the aqueous phase to the solvent phase. The two phases are then efficiently separated by a Podbielniak Model D-36 operating at 200 rpm generating centrifugal forces up to 2000 G's in the extractor. The thienamycin-containing solvent phase, the rich DNNS/solvent stream, is then pumped at 30 gallons per minute to a second extractor where it is contacted with an aqueous buffer, 6% v/v pyridine containing 5 g./liter Na phosphate dibasic, for the back extraction. The back extractant is fed at the rate of 30 gallons per minute to the extractor being used for the back extraction.

About 98% of the thienamycin is extracted from the broth into the DNNS/n-butanol phase in the first extractor and about 95% of the thienamycin is extracted from the DNNS/n-butanol phase into the aqueous buffer using the second extractor. Thus, the overall thienamycin recovery is about 93% from broth into aqueous buffer via the liquid cation exchange process.

The aqueous back extractant from the liquid cation exchange process is now mixed with 2.5 normal sodium hydroxide to bring the pH to 11 using an in-line mixer. This aqueous stream, about 5° C. and pH 11, is fed at 30 gpm to a third extractor when it is intimately contacted with a liquid anion exchanger 30% v/v "Aliquat 336", tricaprylyl methyl ammonium acetate (acetate cycle), in n-butanol which is being fed at 30 gpm. The anion exchange reaction occurs between the negative acetate ion of the "Aliquat 336" moiety and the carboxylate anion form of thienamycin resulting in the transfer of thienamycin from the aqueous phase to the solvent phase. The two phases are then efficiently separated by the centrifugal forces operative in the extractor. The thienamycin containing solvent phase, the rich Aliquat/solvent stream, is then pumped to a fourth extractor where it is contacted with an aqueous buffer, 0.40 molar potassium acetate (pH 5.0) and again, via anion exchange reactions, the thienamycin is transferred, this time from the solvent phase to the aqueous buffer phase. The spent solvent phase, containing the "Aliquat 336" is then continuously regenerated to the acetate cycle using conventional liquid extraction columns.

By this procedure described, about 80 to 85% of the thienamycin is transferred from the feed aqueous stream to the back extractant buffer via the liquid anion exchange process.

Substantial purification of the thienamycin results. Purity refers to the ratio of thienamycin titer to the total dissolved solids titer. In the Example, the purity was increased 30 fold.

If desired, the thienamycin containing extract from the liquid anion exchange process is pH adjusted to 7–7.2 and concentrated to a volume of 20 gal. which is then applied to a 100-gal. Amberlite XAD-2 column at a rate of 2.5 gal./min. The resin is eluted with deionized water at 5 gal./min. and a 150-gal. rich cut is collected and concentrated to 2.5 liters which is then applied to 40 liters of Dowex 50×2 (Na$^+$ cycle) resin at a rate of 600 ml/min. The resin is then eluted at 600 ml./min. with deionized water and a 17-gallon rich cut collected and concentrated to 0.06 gal. which is applied to a 30-liter bed of Bio-Gel P-2 (200–400 mesh) previously equilibrated with 0.1M 2,6-lutidine acetate pH 7.0 buffer. The gel is then developed with the same buffer. The rich cut is concentrated to 0.05 gallons and applied to 4 liters of Amberlite XAD-2 resin. The rich eluate is concentrated and the concentrate freeze-dried yielding thienamycin, about 90% pure.

What is claimed is:

1. A process for recovering the antibiotic thienamycin from fermentation broths or solutions containing said antibiotic which comprises (a) contacting said broths or solution, acidified to a pH of 2.4–4.5, with a water insoluble liquid ion exchanger which is dinonyl naphthalene sulfonic acid, or didodecylnaphthalene sulfonic acid, the exchanger being dissolved (2–15% by volume) in an organic solvent which is an alcohol of 4–10 carbon atoms, a ketone of 4–8 carbon atoms, or an ester of 4–10 carbon atoms, to extract the thienamycin; followed by (b) contacting the liquid ion exchanger system containing the thienamycin with an aqueous sodium bicarbonate, ammonium hydroxide sodium phosphate, potassium phosphate, or pyridine buffer solution to extract the thienamycin; followed by (c)

contacting the aqueous extractant from the previous step, made alkaline to a pH of about 11, with a water insoluble liquid ion exchanger which is tricaprylyl methyl ammonium acetate, tricaprylyl methyl ammonium acetate, tricaprylyl methyl ammonium phosphate, tricaprylyl methyl ammonium propionate, or tricaprylyl methyl ammonium sulfate, in 5-30% by volume solution with said organic solvent of step (a); thereafter, (d) extracting this liquid ion exchanger system with an aqueous sodium acetate, potassium acetate, potassium chloride, hydrogen chloride, or sodium citrate buffer such as; and recovering the thienamycin.

2. The process of claim 1 in which the steps (a) and (b) are employed without additional extraction steps.

3. The process of claim 1 in which the steps (c) and (d) are employed without additional extraction steps.

4. The process of claim 1 in which the steps (c) and (d) are employed first, followed by steps (a) and (b).

UNITED STATES PATENT AND TRADEMARK OFFICE
CERTIFICATE OF CORRECTION

PATENT NO. : 4,168,268

DATED : September 18, 1979

INVENTOR(S) : Rathin Datta et al.

It is certified that error appears in the above-identified patent and that said Letters Patent are hereby corrected as shown below:

In claim 1, line 9, Col. 7 through Col. 8, line 2, subparagraph (d) should read as follows:

-- (d) extracting this liquid ion exchanger system with an aqueous buffer such as sodium acetate, potassium acetate, potassium chloride, hydrogen chloride, or sodium citrate; and recovering the thienamycin. --

Signed and Sealed this

Eighth Day of January 1980

[SEAL]

Attest:

SIDNEY A. DIAMOND

Attesting Officer

Commissioner of Patents and Trademarks